United States Patent [19]
Olinger et al.

[11] Patent Number: 6,160,189
[45] Date of Patent: Dec. 12, 2000

[54] REDUCING THE MONOVINYL ACETYLENE AND/OR BUTADIENE CONTENT OF IMPURE VINYL CHLORIDE

[75] Inventors: Ronald D. Olinger, Lake Charles; Michael B. Guidry, Sulphur, both of La.

[73] Assignee: PPG Industries Ohio, Inc., Cleveland, Ohio

[21] Appl. No.: 08/433,272

[22] Filed: May 2, 1995

[51] Int. Cl.$^7$ ................................................... C07C 17/38
[52] U.S. Cl. ................................................................ 570/238
[58] Field of Search .................................. 570/238

[56] References Cited

U.S. PATENT DOCUMENTS

| | | | |
|---|---|---|---|
| 3,125,607 | 3/1964 | Keating et al. | 260/656 |
| 3,142,709 | 7/1964 | Gause et al. | 260/656 |
| 3,723,550 | 3/1973 | McFadden | 260/656 R |
| 3,876,714 | 4/1975 | Coppens | 260/656 R |
| 3,920,761 | 11/1975 | Krome | 260/656 R |
| 4,760,206 | 7/1988 | Schneider | 570/220 |

*Primary Examiner*—Alan Siegel
*Attorney, Agent, or Firm*—George D. Morris

[57] ABSTRACT

Monovinyl acetylene and/or butadiene are/is removed from impure vinyl chloride by contacting the impure vinyl chloride and substantially anhydrous hydrogen chloride with a catalyst system in which Lewis Acid is carried on an alumina substrate. The preferred Lewis Acid is ferric chloride.

28 Claims, No Drawings

REDUCING THE MONOVINYL ACETYLENE AND/OR BUTADIENE CONTENT OF IMPURE VINYL CHLORIDE

TECHNICAL FIELD

This invention addresses the problem of monovinyl acetylene and butadiene which often appear as impurities in vinyl chloride, and it provides a method for reducing the concentrations of such impurities in the vinyl chloride.

BACKGROUND OF THE INVENTION

Purchasing specifications for vinyl chloride commonly call for monovinyl acetylene ("MVA") and butadiene ("BDE") in amounts, for example, of less than ten parts per million because these impurities have been found to cause difficulties in the polymerization or copolymerization of the vinyl chloride and/or in the polymeric products made in their presence. Thus it is necessary for producers of vinyl chloride to use manufacturing processes which will not generate the undesired amounts of the impurities, and/or to develop methods of removing or reducing the concentration to acceptable levels, which is the subject of the present invention.

U.S. Pat. No. 3,142,709 discloses a method of purifying vinyl chloride containing butadiene as an impurity, wherein the vinyl chloride is treated with anhydrous hydrogen chloride. Contacting vinyl chloride contaminated with butadiene and monovinyl acetylene with catalytic amounts of Lewis acids such as $AlCl_3$ and $FeCl_3$ was disclosed in U.S. Pat. No. 3,723,550. Products of this process are described as heavies which can be removed relatively easily by distillation or other conventional means, in contrast to the monomeric butadiene and other $C_4$'s which are extremely difficult to remove by distillation. In U.S. Pat. No. 4,760,206 which discloses reacting the butadiene present in a vinyl chloride stream with chlorine in the presence of ferric chloride, the ferric chloride is said to polymerize butadiene in vinyl chloride (column 2, lines 20–30); however, if the ferric chloride itself becomes a contaminant in the vinyl chloride, it will interfere with the polymerization of the vinyl chloride (column 1, lines 25–26). Molecular chlorine is also discussed as a decontaminant in U.S. Pat. No. 3,125,607 (see especially Example 2); U.S. Pat. Nos. 3,876,714; and 3,920,761.

Difficulties encountered in attempts to design an improved method of removing the impurities butadiene and/or monovinyl acetylene include not only the known tendency of ferric chloride to be carried over in the treated stream, but also that vinyl chloride can react with hydrogen chloride to produce 1,1-dichloroethane, another compound not wanted in the purified vinyl chloride.

SUMMARY OF THE INVENTION

We have found that, while ferric chloride tends to separate from a silica or clay support and be carried off into the product stream where it may cause complications, it remains relatively stable on an alumina support. We have also found that our objective of reducing the content of monovinyl acetylene and/or butadiene in impure vinyl chloride may be accomplished when the impure vinyl chloride and substantially anhydrous hydrogen chloride are mutually contacted with a catalyst system in which ferric chloride is carried on an alumina substrate. The invention is a liquid phase reaction and is applicable in several contexts which may or may not overlap. These contexts and their relation to the invention may be stated as follows:

In the method wherein impure vinyl chloride containing a contaminating amount of monovinyl acetylene is contacted with catalyst comprising ferric chloride to produce purified vinyl chloride containing a reduced amount of monovinyl acetylene, the invention is the improvement wherein the catalyst is a catalyst system in which the ferric chloride is carried on an alumina substrate and wherein the impure vinyl chloride and substantially anhydrous hydrogen chloride are mutually contacted with the catalyst system.

In the method wherein impure vinyl chloride containing a contaminating amount of butadiene is contacted with catalyst comprising ferric chloride to produce purified vinyl chloride containing a reduced amount of butadiene, the invention is the improvement wherein the catalyst is a catalyst system in which the ferric chloride is carried on an alumina substrate and wherein the impure vinyl chloride and substantially anhydrous hydrogen chloride are mutually contacted with the catalyst system.

In the method wherein impure vinyl chloride containing contaminating amounts of butadiene and monovinyl acetylene is contacted with catalyst comprising ferric chloride to produce purified vinyl chloride containing reduced amounts of butadiene and monovinyl acetylene, the invention is the improvement wherein the catalyst is a catalyst system in which the ferric chloride is carried on an alumina substrate and wherein the impure vinyl chloride and substantially anhydrous hydrogen chloride are mutually contacted with the catalyst system.

In carrying out the present invention, the residence times and other conditions are preferably, but not necessarily, controlled to minimize the formation of 1,1-dichloroethane. Although it is not desired to be bound by any theory, it is believed that hydrochlorinated impurities generated by the process are compounds having significantly higher boiling points than vinyl chloride. These higher boiling compounds are known as "heavies". Vinyl chloride is easily separated from the heavies by distillation or other conventional techniques.

Our invention broadly includes using in the process described any stable combination of a Lewis Acid on an alumina support, the combination remaining substantially stable under the process conditions. Examples of such Lewis Acids include ferric chloride and aluminum trichloride. Additional examples of Lewis Acids are given in U.S. Pat. No. 3,723,550 at column 1, lines 41–48. Therefore, broadly, in the method wherein impure vinyl chloride containing a contaminating amount of butadiene, monovinyl acetylene, or both butadiene and monovinyl acetylene, is contacted with catalyst comprising Lewis Acid to produce purified vinyl chloride containing a reduced amount of butadiene or monovinyl acetylene or both butadiene and monovinyl acetylene, the invention is the improvement wherein the catalyst is a catalyst system in which the Lewis Acid is carried on an alumina substrate and wherein the impure vinyl chloride and substantially anhydrous hydrogen chloride are mutually contacted with the catalyst system.

DETAILED DESCRIPTION OF THE INVENTION

Our ferric chloride catalyst can be made by preparing a slurry of ferric chloride and alumina, gently heating while stirring it to remove water, and drying it. Usually the catalyst system has an iron content of from 1 to 10 percent by weight. We prefer that the catalyst system have an iron content of from 3 to 8 percent by weight. Generally more than 10 percent by weight is not necessary, and if more than 15 percent by weight is used, there is a risk that ferric chloride in detrimental amounts will unnecessarily leach off and enter the process stream.

The monovinyl acetylene and butadiene contents of the freshly produced impure vinyl chloride streams on which our invention is most often employed may vary considerably. In most instances, however, the impure vinyl chloride will contain from 1 ppm to 100 ppm of monovinyl acetylene. Often the impure vinyl chloride will contain from 1 ppm to 20 ppm of monovinyl acetylene. Commonly the impure vinyl chloride will contain from 5 ppm to 10 ppm of monovinyl acetylene. Usually the impure vinyl chloride will contain from 2 ppm to 100 ppm of butadiene. Frequently the impure vinyl chloride will contain from 3 ppm to 20 ppm of butadiene. In many cases the impure vinyl chloride will contain from 4 ppm to 8 ppm of butadiene.

The amount of substantially anhydrous hydrogen chloride present in the impure vinyl chloride may vary widely. If the substantially anhydrous hydrogen chloride is not already present in the impure vinyl chloride in sufficient amount, substantially anhydrous hydrogen chloride may be added. Usually substantially anhydrous hydrogen chloride is present in an amount of from 0.05 to 6 percent by weight of the impure vinyl chloride. The substantially anhydrous hydrogen chloride is often be present in an amount of from 0.05 to 0.50 percent by weight; more than 1 percent by weight is not necessary, but up to 6 percent by weight or more is not detrimental. The substantially anhydrous hydrogen chloride content of an impure vinyl chloride plant stream is normally in the range of from 2 to 6 percent by weight, and this is more than adequate for our purposes. Our invention is quite effective whether the substantially anhydrous hydrogen chloride is already present in the impure vinyl chloride, as is commonly the case with freshly produced vinyl chloride, or whether it is added at any point up to the point of contact with the supported Lewis acid. As used herein and in the claims "substantially anhydrous" means less than 100 ppm of water.

The pressures at which the the impure vinyl chloride and the substantially anhydrous hydrogen chloride are mutually contacted with the catalyst system may vary widely. In most instances the pressures are in the range of from 0 to 1500 kPa, gauge. From 200 to 1100 kPa, gauge is preferred.

The temperatures at which the the impure vinyl chloride and the substantially anhydrous hydrogen chloride are mutually contacted with the catalyst system may also be widely varied. Usually the temperatures are in the range of from 25° C. to 80° C. From 30° C. to 65° C. is preferred.

The invention is further described in conjunction with the following Examples which are to be considered illustrative rather than limiting, and in which all parts by weight and all percentages are percentages by weight unless otherwise specified. In each of the runs described in the Examples, the impure vinyl chloride feedstock stream composition was not constant throughout the duration of the run, but varied somewhat. In general the impure vinyl chloride feedstock streams used in the Examples contained from 5 to 12 ppm monovinyl acetylene, from 4 to 8 ppm butadiene, and from 2 to 6 percent by weight hydrogen chloride. In the various Tables, the following abbreviations have the following meanings: BDE is butadiene; MVA is monovinyl acetylene; DCE is 1,1-dichloroethane; TEMP is temperature; PRESS is gauge pressure; Lpm is liters per minute; NA is not analyzed; and ND is none detected, i.e., <0.01 ppm.

EXAMPLE 1

A first reactor comprised a flanged inlet section, a central section, and a flanged outlet section. The central section comprised a length of carbon steel pipe having an internal diameter of 3.81 centimeters and provided with flanges on both ends such that the distance between the faces of the flanges was 1.524 meters. Wire screening was placed between the mating flanges of the inlet section and the central section and the flanges were bolted together. Catalyst was added to substantially fill the central section, wire screening was placed between the mating flanges of the central section and the outlet section, and the flanges were bolted together.

Table 1 shows the results obtained using as catalyst ferric chloride on alumina containing 7 percent iron by weight (Discovery Chemical Company, Port Allen, Tex.).

TABLE 1

| | PRODUCT STREAM | | | | | | CUMULATIVE | |
| --- | --- | --- | --- | --- | --- | --- | --- | --- |
| DAY | BDE ppm | MVA ppm | DCE ppm | TEMP ° C. | PRESS kPa | FLOW Lpm | VOLUME liters | REMARKS |
| 0 | | | | * | 207 | 3.785 | 0 | START |
| 1 | ND | ND | ND | * | 207 | 3.785 | 5451 | |
| 5 | 0.1 | 2.3 | 590 | * | 207 | 3.785 | 10902 | |
| 6 | 0.2 | 3.0 | 1660 | * | 207 | 3.785 | 16353 | |
| 7 | 0.2 | 2.6 | 1769 | * | 207 | 3.785 | 21804 | |
| 11 | 1.0 | 5.8 | ND | * | 207 | 3.785 | 43608 | END |

NOTE
* = 43° C. to 50° C.;

EXAMPLE 2

The first reactor was modified by adding a steam jacket to provide heating. A smaller rotameter was installed to obtain lower flows, and a filter added to remove the carbonaceous fines found in the absorber bottoms feed.

The central section of the modified first reactor was substantially filled with catalyst which was ferric chloride on alumina containing 3.7 percent iron by weight (Discovery Chemical Company, Port Allen, Tex.). Table 2 shows the results obtained using this catalyst. Before the first day of the run had been completed, a sample of the product stream was analyzed: BDE and MVA were not detected and DCE was found to be present at a concentration of 1.14 percent.

TABLE 2

| | PRODUCT STREAM | | | | | CUMULATIVE | |
|---|---|---|---|---|---|---|---|
| DAY | BDE ppm | MVA ppm | DCE ppm | TEMP °C. | PRESS kPa | FLOW Lpm | VOLUME liters | REMARKS |
| 0 | | | | * | 207 | 3.785 | 0 | START |
| 3 | 0.99 | 2.99 | 699 | * | 207 | 3.785 | 16353 | |
| 4 | 0.10 | 0.94 | 284 | 52 | 207 | 1.438 | 18424 | |
| 6 | 2.12 | 3.18 | 262 | 32 | 207 | 1.438 | 22565 | |
| 10 | 0.56 | 4.20 | 1805 | 46 | 207 | 0.795 | 27145 | |
| 13 | 0.59 | 3 50 | 444 | 52 | 207 | 0.795 | 30578 | |
| 17 | 0.21 | 2.96 | 944 | 43 | 207 | 0.795 | 35158 | |
| 19 | 0.16 | 3.15 | 506 | 35 | 207 | 0.795 | 37448 | END |

NOTE
* = 43° C. to 50° C.;

EXAMPLE 3

The catalyst in the modified first reactor was replaced with another catalyst which was ferric chloride on alumina containing 7 percent iron by weight (Discovery Chemical Company, Port Allen, Tex.). This catalyst was from a lot different than that used in Example 1. Table 3 shows the results obtained using this catalyst.

TABLE 3

| | PRODUCT STREAM | | | | | CUMULATIVE | |
|---|---|---|---|---|---|---|---|
| DAY | BDE ppm | MVA ppm | DCE ppm | TEMP °C. | PRESS kPa | FLOW Lpm | VOLUME liters | REMARKS |
| 0 | | | | 49 | 414 | 1.514 | 0 | START |
| 4 | ND | 1.80 | ND | 46 | 483 | 1.514 | 8722 | |
| 6 | 1.53 | 3.03 | 500 | 49 | 483 | 1.514 | 13083 | |
| 10 | 0.49 | 3.90 | 381 | 49 | 483 | 0.946 | 18534 | |
| 12 | 0.73 | 4.31 | 677 | 49 | 607 | 0.946 | 21259 | |
| 14 | 0.27 | 3.91 | 536 | 53 | 586 | 0.606 | 23004 | |
| 17 | 0.98 | 3.40 | 476 | 51 | 510 | 0.303 | 24314 | |
| 20 | 0.20 | 0.92 | 273 | 57 | 552 | 0.303 | 25624 | STOP |
| 27 | | | | 60 | 593 | 0.606 | 25624 | RESUME |
| 31 | 0.20 | 3.89 | 717 | 62 | 593 | 0.606 | 29114 | |
| 34 | 0.20 | 4.85 | 811 | 60 | 593 | 0.606 | 31730 | |
| 39 | 0.90 | 3.20 | 656 | 60 | 965 | 0.606 | 36091 | END |

EXAMPLE 4

The catalyst in the modified first reactor was replaced with another catalyst which was ferric chloride on 1.59 millimeter alumina extrudates and which contained 5 percent iron by weight (Engelhard Company, Beachwood, Ohio). Table 4 shows the results obtained using this catalyst.

TABLE 4

| | PRODUCT STREAM | | | | CUMULATIVE | |
|---|---|---|---|---|---|---|
| DAY | BDE ppm | MVA ppm | TEMP °C. | PRESS kPa | FLOW Lpm | VOLUME liters | REMARKS |
| 0 | | | 60 | 896 | 0.681 | 0 | START |
| 1 | ND | 0.20 | 60 | 896 | 0.681 | 980 | |
| 3 | NA | NA | 60 | 896 | 0.681 | 2945 | STOP |
| 4 | | | 54 | 855 | 0.681 | 2945 | RESUME |
| 5 | ND | 0.66 | 54 | 855 | 0.681 | 3925 | |
| 13 | ND | 2.12 | 59 | 827 | 0.681 | 11768 | |
| 18 | 0.35 | 2.54 | 62 | 869 | 0.681 | 16670 | END |

Before the twenty-seventh day had been completed, a sample of the product stream was analyzed with the following results: 0.06 ppm BDE, 0.49 ppm MVA, and 856 ppm DCE.

EXAMPLE 5

A second reactor comprised a flanged inlet section, a central section, and a flanged outlet section. The central section comprised a length of mild steel pipe having an internal diameter of 20.32 centimeters and provided with flanges on both ends such that the distance between the faces of the flanges was 3.048 meters. Wire screening was placed between the mating flanges of the inlet section and the central section and the flanges were bolted together. Catalyst was added to substantially fill the central section, wire screening was placed between the mating flanges of the central section and the outlet section, and the flanges were bolted together.

Table 5 shows the results obtained using as catalyst ferric chloride on alumina containing 7 percent iron by weight (Discovery Chemical Company, Port Allen, Tex.).

TABLE 5

| | PRODUCT STREAM | | | | | CUMULATIVE | | |
|---|---|---|---|---|---|---|---|---|
| DAY | BDE ppm | MVA ppm | DCE ppm | TEMP °C. | PRESS kPa | FLOW Lpm | VOLUME liters | REMARKS |
| 0 | | | | 38 | 758 | 3.028 | 0 | START |
| 1 | ND | ND | 748 | 38 | 758 | 3.028 | 4361 | |
| 2 | NA | NA | NA | 38 | 758 | 7.571 | 15263 | |
| 3 | ND | ND | 317 | 43 | 758 | 7.571 | 26165 | |
| 7 | 1.65 | 3.95 | 1159 | 38 | 758 | 7.571 | 69773 | |
| 10 | 0.20 | Trace | 723 | 38 | 758 | 7.571 | 102479 | |
| 14 | 0.15 | Trace | 1448 | 32 | 758 | 7.571 | 146087 | |
| 17 | 0.92 | 3.10 | 4065 | 37 | 738 | 7.571 | 178793 | |
| 21 | ND | Trace | 635 | 38 | 827 | 7.571 | 222401 | |
| 24 | 0.48 | Trace | 1383 | 38 | 814 | 7.571 | 255107 | |
| 28 | 0.90 | 3.10 | 1680 | 38 | 827 | 7.571 | 298715 | |
| 31 | 0.40 | 0.60 | 735 | 43 | 814 | 6.814 | 328150 | |
| 35 | ND | 0.65 | 759 | 43 | 827 | 6.814 | 367397 | |
| 38 | 0.52 | 2.95 | 785 | 43 | 827 | 6.814 | 369832 | |
| 42 | 2.02 | 3.25 | 990 | 48 | 758 | 6.814 | 436079 | |
| 45 | 0.20 | Trace | 1241 | 53 | 814 | 6.814 | 465514 | |
| 49 | 0.26 | ND | 1547 | 53 | 758 | 7.571 | 509122 | |
| 52 | 0.13 | Trace | 1543 | 53 | 786 | 7.571 | 541828 | |
| 56 | Trace | ND | 372 | 52 | 814 | 6.814 | 581075 | |
| 59 | 0.06 | Trace | 323 | 52 | 793 | 5.678 | 605604 | |
| 63 | ND | 1.00 | 951 | 54 | 786 | 5.678 | 638310 | |
| 66 | ND | ND | 1405 | 54 | 800 | 5.678 | 662839 | |
| 70 | 0.14 | ND | 1362 | 52 | 689 | 6.814 | 702086 | |
| 73 | ND | 0.91 | 1501 | 49 | 689 | 5.678 | 726615 | |
| 77 | 0.15 | ND | 1081 | 49 | 676 | 3.785 | 748419 | STOP |
| 98 | | | | 49 | 848 | 11.356 | 748419 | RESUME |
| 100 | 0.30 | Trace | 152 | 49 | 848 | 11.356 | 781125 | |
| 105 | ND | 0.70 | 1423 | 49 | 855 | 11.356 | 862890 | |
| 108 | 0.11 | 0.93 | 1301 | 43 | 827 | 18.927 | 944655 | |
| 112 | ND | Trace | 767 | 47 | 827 | 17.413 | 1044953 | |
| 115 | ND | Trace | 1700 | 46 | 800 | 15.142 | 1110365 | |
| 119 | ND | Trace | 601 | 46 | 820 | 13.249 | 1186679 | |
| 122 | 0.24 | 1.12 | 1157 | 43 | 807 | 11.356 | 1235738 | |
| 126 | 0.12 | Trace | 421 | 44 | 669 | 9.464 | 1290248 | END |

EXAMPLE 6

The catalyst in the second reactor was replaced with another catalyst which was ferric chloride on alumina containing 7.4 percent iron by weight (YS Incorporated, Collinsville, Ala.). Table 6 shows the results obtained using this catalyst.

TABLE 6

| | PRODUCT STREAM | | | | | CUMULATIVE | | |
|---|---|---|---|---|---|---|---|---|
| DAY | BDE ppm | MVA ppm | DCE ppm | TEMP °C. | PRESS kPa | FLOW Lpm | VOLUME liters | REMARKS |
| 0 | | | | 41 | 869 | 13.249 | 0 | START |
| 3 | ND | ND | | 41 | 869 | 13.249 | 57235 | |
| 4 | 0.10 | ND | 255 | 41 | 648 | 7.571 | 68137 | |
| 8 | 0.54 | 2.11 | 616 | 39 | 648 | 15.142 | 155353 | |
| 9 | NA | NA | NA | 39 | 648 | 15.142 | 155353 | STOP |
| 17 | | | | 44 | 793 | 9.464 | 155353 | RESUME |

TABLE 6-continued

| | PRODUCT STREAM | | | | | | CUMULATIVE | |
| --- | --- | --- | --- | --- | --- | --- | --- | --- |
| DAY | BDE ppm | MVA ppm | DCE ppm | TEMP °C. | PRESS kPa | FLOW Lpm | VOLUME liters | REMARKS |
| 18 | 0.70 | 0.71 | 1099 | 44 | 793 | 9.463 | 168980 | |
| 21 | ND | 0.87 | 422 | 43 | 786 | 10.769 | 215503 | END |

It may be observed from the above data that a new bed of ferric chloride on alumina will proceed through an initial conditioning period and then gradually improve in efficiency.

Although the present invention has been described with reference to specific details of certain embodiments thereof, it is not intended that such details should be regarded as limitations upon the scope of the invention except insofar as they are included in the accompanying claims.

We claim:

1. In the method wherein impure vinyl chloride containing a contaminating amount of monovinyl acetylene is contacted with catalyst comprising ferric chloride to produce purified vinyl chloride containing a reduced amount of monovinyl acetylene, the improvement wherein the catalyst is a catalyst system in which the ferric chloride is carried on an alumina substrate and wherein the impure vinyl chloride and substantially anhydrous hydrogen chloride are mutually contacted with the catalyst system.

2. The method of claim 1 wherein said impure vinyl chloride initially contains from 1 ppm to 100 ppm of monovinyl acetylene.

3. The method of claim 1 wherein the substantially anhydrous hydrogen chloride is present in an amount of from 0.05 to 6 percent by weight of the impure vinyl chloride.

4. The method of claim 1 wherein the contacting is effected by passing said substantially anhydrous hydrogen chloride and a stream of said impure vinyl chloride through a bed of said catalyst system.

5. The method of claim 1 wherein the contacting takes place at temperatures in the range of from 25° C. to 80° C. and at pressures in the range of from 0 to 1500 kPa, gauge.

6. The method of claim 1 wherein the catalyst system has an iron content of from 1 to 10 percent by weight.

7. The method of claim 1 wherein the the catalyst system has an iron content of from 3 to 8 percent by weight.

8. The method of claim 1 wherein said substantially anhydrous hydrogen chloride is in admixture with said impure vinyl chloride.

9. The method of claim 1 wherein said purified vinyl chloride contains heavies and wherein vinyl chloride is separated from said heavies by distillation.

10. In the method wherein impure vinyl chloride containing a contaminating amount of butadiene is contacted with catalyst comprising ferric chloride to produce purified vinyl chloride containing a reduced amount of butadiene, the improvement wherein the catalyst is a catalyst system in which the ferric chloride is carried on an alumina substrate and wherein the impure vinyl chloride and substantially anhydrous hydrogen chloride are mutually contacted with the catalyst system.

11. The method of claim 10 wherein said impure vinyl chloride initially contains from 2 ppm to 100 ppm butadiene.

12. The method of claim 10 wherein the substantially anhydrous hydrogen chloride is present in an amount of from 0.05 to 6 percent by weight of the impure vinyl chloride.

13. The method of claim 10 wherein the contacting is effected by passing said substantially anhydrous hydrogen chloride and a stream of said impure vinyl chloride through a bed of said catalyst system.

14. The method of claim 10 wherein the contacting takes place at temperatures in the range of from 25° C. to 80° C. and at pressures in the range of from 0 to 1500 kPa, gauge.

15. The method of claim 10 wherein the catalyst system has an iron content of from 1 to 10 percent by weight.

16. The method of claim 10 wherein the the catalyst system has an iron content of from 3 to 8 percent by weight.

17. The method of claim 10 wherein said substantially anhydrous hydrogen chloride is in admixture with said impure vinyl chloride.

18. The method of claim 10 wherein said purified vinyl chloride contains heavies and wherein vinyl chloride is separated from said heavies by distillation.

19. In the method wherein impure vinyl chloride containing contaminating amounts of butadiene and monovinyl acetylene is contacted with catalyst comprising ferric chloride to produce purified vinyl chloride containing reduced amounts of butadiene and monovinyl acetylene, the improvement wherein the catalyst is a catalyst system in which the ferric chloride is carried on an alumina substrate and wherein the impure vinyl chloride and substantially anhydrous hydrogen chloride are mutually contacted with the catalyst system.

20. The method of claim 19 wherein said impure vinyl chloride initially contains from 1 ppm to 100 ppm of monovinyl acetylene and from 2 ppm to 100 ppm of butadiene.

21. The method of claim 19 wherein the substantially anhydrous hydrogen chloride is present in an amount of from 0.05 to 6 percent by weight of the impure vinyl chloride.

22. The method of claim 19 wherein the contacting is effected by passing said substantially anhydrous hydrogen chloride and a stream of said impure vinyl chloride through a bed of said catalyst system.

23. The method of claim 19 wherein the contacting takes place at temperatures in the range of from 25° C. to 80° C. and at pressures in the range of from 0 to 1500 kPa, gauge.

24. The method of claim 19 wherein the catalyst system has an iron content of from 1 to 10 percent by weight.

25. The method of claim 19 wherein the the catalyst system has an iron content of from 3 to 8 percent by weight.

26. The method of claim 19 wherein said substantially anhydrous hydrogen chloride is in admixture with said impure vinyl chloride.

27. The method of claim 19 wherein said purified vinyl chloride contains heavies and wherein vinyl chloride is separated from said heavies by distillation.

28. In the method wherein impure vinyl chloride containing a contaminating amount of butadiene, monovinyl acetylene, or both butadiene and monovinyl acetylene, is contacted with catalyst comprising Lewis Acid to produce purified vinyl chloride containing a reduced amount of butadiene or monovinyl acetylene or both butadiene and monovinyl acetylene, the improvement wherein the catalyst is a catalyst system in which the Lewis Acid is carried on an alumina substrate and wherein the impure vinyl chloride and substantially anhydrous hydrogen chloride are mutually contacted with the catalyst system.

* * * * *